US005585346A

United States Patent [19]
Malech et al.

[11] Patent Number: 5,585,346
[45] Date of Patent: *Dec. 17, 1996

[54] PEPTIDE DERIVATIVES OF CYTOCHROME $B_{558}$ AND THEIR USE AS MEDICAMENTS

[75] Inventors: Harry L. Malech, Bethesda; Karen J. Lomax, Silver Spring; Daniel Rotrosen, Takoma Park; Hiroyuki Nunoi, Rockville, all of Md.

[73] Assignee: The United States of America as represented by the Department of Health and Human Services, Washington, D.C.

[ * ] Notice: The portion of the term of this patent subsequent to May 24, 2010, has been disclaimed.

[21] Appl. No.: 331,652

[22] Filed: Mar. 31, 1989

[51] Int. Cl.$^6$ .......................... A61K 38/00; C07K 14/00; C07K 7/08; C07K 7/06
[52] U.S. Cl. .................. 514/12; 514/13; 514/14; 514/15; 514/16; 530/324; 530/325; 530/326; 530/328; 530/329
[58] Field of Search ....................................... 530/325–326, 530/328, 327, 324; 514/13, 14–16

[56] References Cited

PUBLICATIONS

Rotrosen et al, "A cytoplasmic carboxylterminal . . . ," *Clin. Res.*, vol. 36, No. 3, Apr. 1988.
Rotrosen, et al, *J. Biol. Chem*, vol. 265, No. 32, pp. 19910–19915, 1990.
Levy, *Biochem. and Biophysc., Res. Comm*, vol. 170, No. 3, 1990.
Rotrosen, et al, *J. Biological Chem*, vol. 265, pp. 8745–8750, 1990.
Kleinberg, et al, *Biochemistry* vol. 31, 1992, 2686–2690.
Kleinberg, et al, J. Biol Chem, vol. 265, No, 26, 1990, pp. 15577–15583.
Grynkiewicz, et al, *J. Biol. Chem*, vol. 260., No. 6, pp. 3440–3450, 1985.
Rotrosen, et al, (Clinical Research, 582 A).
Iizuka, et al., "Pyridine and Imidazole Reversibly Inhibit the Respiratory Burst of Porcine and Human Neutrophils", *Biochem and Biophysic Res Comm*. vol. 130 (2) pp. 621–626 1985.
Kleinberg, et al., "Glycosylation of Cytochrome b558 Large Subunit Varies in Different Human Phagocytic Cells", vol. 143, pp. 4152–4157, 1989.
Yamaguchi, et al., "Purification and Some Properties of the Small Subunit of Cytochrome b558 from Neutrophils", *J. Biol. Chem.*, vol. 264(1) pp. 112–118, 1989.
Verhoeven, et al., "Characterization of Two Monoclonal Antibodies Against Cytochrome b558 of Human Neutrophils," *Blood*, vol. 73, (6) pp. 1686–1694, 1989.
Royer–Pokora, et al, "Cloning the gene for an inherited human disorder–chronic granulomatous disease–on the basis of its chromosomal location", Nature, vol. 322, pp. 32–38, 1986.
Pember, et al., "Cytochrome b558 from (Bovine) Granulocytes" vol. 259, *J. Biol. Chem.* pp. 10590–10595, 1984.
Lutter, et al., "Purification and Partial Characterization of the b–type Cytochrome from Human Polymorphonuclear Leukocytes", *J. Biol. Chem* vol. 260 (4), pp. 2237–2244, 1985.
Parkos, et al., "Purified Cytochrome b from Human Granulocyte Plasma Membrane is comprised of two polypeptides with Relative Molecular Weights of 91,000 and 22,000", J. Clin. Invest, vol. 80, pp. 732–742.

*Primary Examiner*—Elizabeth C. Weimar
*Assistant Examiner*—S. G. Marshall
*Attorney, Agent, or Firm*—Birch, Stewart, Kolasch & Birch, LLP

[57] ABSTRACT

Peptide derivatives with inhibitory activity on the enzyme systems involved in the oxidative burst of human phagocytic cells comprise a certain sequence of a number of carboxyl-terminal amino acids of human cytochrome $b_{558}$. The derivatives may be used in medicaments for the treatment of inflammatory diseases.

17 Claims, 2 Drawing Sheets

PEPTIDE DERIVATIVES OF CYTOCHROME $B_{558}$ AND THEIR USE AS MEDICAMENTS

BACKGROUND OF THE INVENTION

1. Field of the Invention

The present invention relates to peptide derivatives with inhibitory activity on the enzyme systems involved in the oxidative burst of human phagocytic cells. More specifically, the invention relates to peptide derivatives comprising a limited number of carboxyl-terminal amino acids of human cytochrome $b_{558}$ which appear to inhibit activation of the respiratory burst of human phagocytic cells, i.e. neutrophils, eosinophils and monocytes. The peptide derivatives are foreseen to be used in medicaments for mammals, including humans, in the treatment of inflammatory diseases.

2. Description of the Technical Background

A large number of anti-inflammatory drugs have been devised which either decrease the accumulation of phagocytic cells at sites of inflammation or decrease the level of activation of phagocytic cells. Such substances include corticosteroids which act on the overall metabolism of cells or nonsteroidal anti-inflammatory drugs such as aspirin, ibuprofen, indomethacin and others which interfere with the metabolism of arachidonic acid. As a result of these actions, they interfere with the accumulation and activation of phagocytic cells. These substances do not have any specificity for phagocytic cells or the functions of phagocytic cells, and the side effects of these agents relate in part to actions on other cell types and organ systems.

SUMMARY OF THE INVENTION

One purpose of this invention is to devise an anti-inflammation substance which would act in a highly specific fashion to inhibit the production of toxic oxygen products (superoxide, hydrogen peroxide, hydroxyl radical and others) by human phagocytic cells and thereby decrease the tissue damage which occurs at sites of inflammation as a result of the action of these oxidative products. An inhibitor whose structure is determined by knowledge of the structure and function of components of the superoxide producing system of human phagocytes is likely to inhibit this system without affecting other phagocytic cell activities or the function of other cell types or organ systems.

It has now, in accordance with the invention, been found that a certain sequence of a number of carboxyl-terminal amino acids of human cytochrome $b_{558}$ (a component of the oxidative burst enzyme system) appears to inhibit activation of the respiratory burst of the human neutrophil, monocyte and eosinophil. The amino acid sequence constituting the peptide derivative competes with native cytochrome $b_{558}$ for binding to other enzymatic components of the phagocytic cell superoxide producing system and thereby prevents activation of NADPH oxidase activity critical to superoxide production. Hence, in its broadest aspect, the invention relates to an optionally substituted peptide derivative which blocks superoxide production in phagocytic cells, containing 6–30 amino acid residues and containing a domain which is identical to a domain of the 91 kDa subunit of human cytochrome $b_{558}$. It is preferred that the peptide contains a sequence of 13–19 amino acids, which sequence is identical to a domain of the carboxyl-terminal peptide position of the 91 kDa subunit of human cytochrome $b_{558}$.

DETAILED DESCRIPTION OF THE INVENTION:

Figure 1:
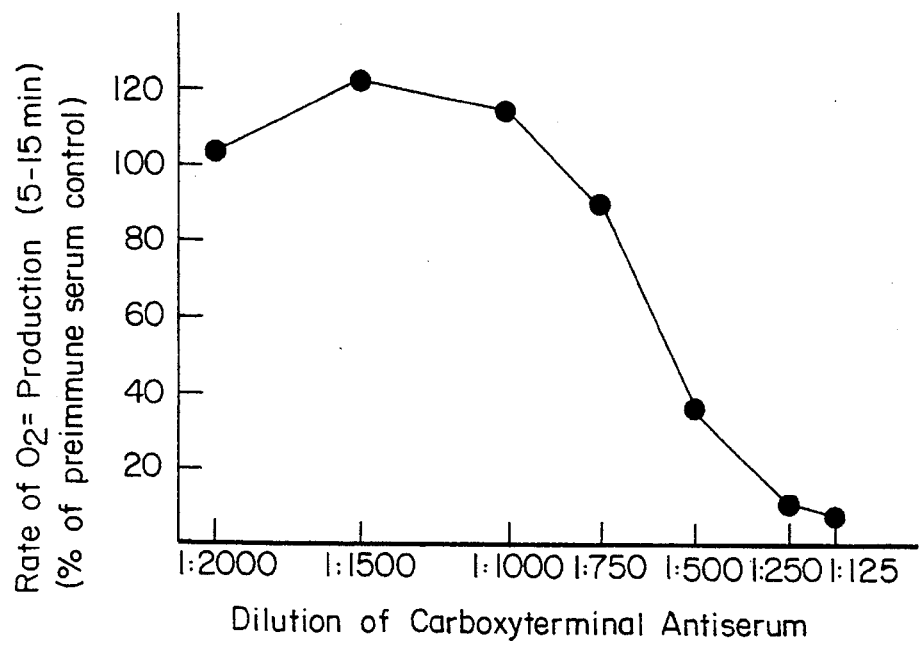

More specifically, the invention relates to an optionally substituted peptide as defined above which is the large subunit of human cytochrome $b_{558}$.

More specifically, this domain of the large subunit of human cytochrome $b_{558}$ is a carboxyl-terminal peptide derivative, which preferably is in unsubstituted form.

The sequence of amino acids is preferably linear and comprises between 6 and 30 amino acid residues, especially 13–20 amino acid residues, specifically 19 amino acid residues.

A preferred sequence of amino acids comprises the following amino acids: Pro-Arg-Gly-Val-His-Phe-Ile-Phe-Asn-Lys-Glu-Asn-Phe.

Another preferred sequence of amino acids comprises the following amino acids: Ser-Asn-Ser-Glu-Ser-Gly-Pro-Arg-Gly-Val-His-Phe-Ile-Phe-Asn-Lys-Glu-Asn-Phe.

It is contemplated that addition of a certain class of chemical moieties selected from the groups comprising hydrophobic and amphipathic groups will enhance the penetration of the peptide derivative into phagocytic cells and/or will assist in the retention of such a substituted derivative of the peptide within phagocytic cells. Examples of such auxiliary groups are cleavable ester groups such as acetoxymethylester which has been used successfully to modify hydrophilic, ionic chemical substances which then may pass through the lipid barrier of the cell exterior and into the inside of living human cells and tissues (Grynkeiwicz G, Poenie M, and Tsien R. The Journal of Biological Chemistry Mar. 25, 1985, 260;3440–3450, 1985). When the derivatives are to be used in warm-blooded animals including human beings, it is appreciated that the derivatization should not render the peptide derivatives toxic. Peptide derivatives with added chemical moieties as defined above are pro-drugs for the active peptide derivatives.

It is contemplated that the mechanism of action is to directly inhibit activation of the specific enzymes involved in the oxidative burst of human phagocytic cells, by binding to critical components of this system within phagocytic cells. Because of this mechanism of action it is contemplated that the peptide derivatives comprising the carboxyl-terminal domain of cytochrome $b_{558}$ will act only on phagocytic cells and specifically decrease production of toxic oxygen products by these cells with a minimum of effects upon other cell types and organ systems.

The mode of action is probably due to a condition in which the peptide derivatives according to the invention dominates the native cytochrome $b_{558}$ in binding to other enzymatic components of the phagocytic cell superoxide producing system and thereby prevents activation of NADPH oxidase activity critical to superoxide production.

Hence, another aspect of the invention relates to a method for directly inhibiting activation of the specific enzyme system involved in the oxidative burst of human phagocytic cells which involves administration of an effective amount of an optionally substituted peptide derivative identical with a domain of the 91 kDa subunit of human cytochrome $b_{558}$ which blocks superoxide production in phagocytic cells.

A further aspect of the invention relates to a method for directly inhibiting activation of the specific enzyme system involved in the oxidative burst of human phagocytic cells which involves administration of an effective amount of optionally substituted peptide derivatives comprising the carboxyl-terminal domain of cytochrome $b_{558}$. The peptide derivatives involved are as described above.

A further aspect of the invention relates to a method for preventing or decreasing the tissue damage associated with phagocyte oxidative burst which involves administration of an optionally substituted peptide derivative as described above. The invention relates specifically to a method for preventing or decreasing symptoms such as gout, autoimmune disorders, myocardial infarction, adult respiratory distress syndrome, asthma and certain dermatological disorders which comprises administering an effective amount of the peptide derivative thereof to a patient in need of such treatment.

A further aspect of the invention relates to a medicament comprising the optionally substituted peptide derivative as described above.

The medicaments according to the invention can be prepared by methods well known in pharmaceutic practice.

The peptide derivatives according to the invention can be formulated into forms for administration to mucous membranes, intraarticular forms for administration into joints, topical cutaneous administration forms such as ointments, solutions, creams and lotions, parenteral preparations such as dispersions and solutions, and inserts such as suppositories; together with suitable carriers, excipients, binders, fillers, etc., into dosage forms each comprising a fraction or a multiplum of the daily dose required in order to achieve the desired result of treatment. While oral delivery may be effective, local delivery of peptide in a carrier to sites of inflammation may be preferred (droplet nebulization of peptide in aqueous or organic carrier [such as dimethyl sulfoxide] for application to mucous membranes or inhalation to lungs; external local application of peptide in aqueous or organic carrier; or injection of peptide in solvent carrier to joints or other sites). For such local application the peptides may be present in carrier at concentrations of 0.01 to 1.0 mg/ml, optimally at 0.1 mg/ml. For injection directly into a joint in a human an indicated daily dose lies in the range of 0.1–3 mg of peptide derivative, preferably 0.5–2.0 mg; said dose can be given in 1–2 ml of carrier. Intravenous delivery of peptide may be required for systemic treatment. For such systemic treatment the amount of active ingredient in each administration form lies between 0.1 and 1 g which may be given in preparations comprising between 1 and 95% by weight of the active ingredient, the balance being the auxiliary agent(s).

Liquid administration forms may be prepared from concentrated forms by adding physiologically acceptable carriers or diluents such as water, saline, glucose solutions, etc., optionally comprising buffering agents and salts rendering the final liquid preparation isotonic.

The peptide may also be incorporated into liposomal vesicles exactly as described for incorporating the antibiotic amphotericin B into lipid vesicles (e.g. as described in the references: Lopez-Berenstein, G., Fainstein, V., Hopfer, R., Mehta K., Sullivan, M. P., Keating, M., Rosenblum, M. G., Mehta, R., Luna, M., Hersh, E. M., Reuben, J., Juliano, R. L., Bodey, G. P. (1985) Liposomal amphotericin B for the treatment of systemic fungal infections in patients with cancer: A preliminary study. *J. Infec. Dis.* 151:704–710; Lopez-Berestein, G. (1987) Liposomes as carriers of antimicrobial agents. *Antimicrob. Agents Chemother.* 31:675–678; Lopez-Berestein, G., Hopfer, R. L., Mehta, R., Mehta, K., Hersh, E. M., Juliano, R. L. (1984) Liposome-encapsulated amphotericin B for the treatment of disseminated candidiasis in neutropenic mice. *J. Infect. Dis.* 150:278–283; and Mehta, R., Lopez-Berestein, G., Hopfer, R., Mills, K., Juliano, R. L. (1984) Liposomal amphotericin B is toxic to fungal cells but not to mammalian cells. *Biochem. Biophys. Acta* 770:230–234). The amount of peptide incorporated into liposomes may be 0.1 mg peptide to 1 mg peptide per mg lipid. The amount of peptide administered in lipid encapsulated form will be identical to the injection route doses indicated above.

The peptide derivatives can be prepared as described in the literature (Lifson J D, Hwang K M, Nara P L, Fraser B, Padgett M, Dunlop N M, Eiden L E. Synthetic CD4 peptide derivatives that inhibit HIV infection and cytopathicity. Science Aug. 5, 1988; 241 (4866):712–6; Lindner W, Robey F A. Automated synthesis and use of N-chloroacetyl-modified peptides for the preparation of synthetic peptide polymers and peptide-protein immunogens. Int J Pept Protein Res Dec. 30, 1987; (6):794–800; Barany G, Kneib-Cordonier N, Mullen DG. Solid-phase peptide synthesis: a silver anniversary report. Int J Pept Protein Res Dec. 30, 1987; (6):705–39; Clark-Lewis I, Aebersold R, Ziltener H, Schrader J W, Hood L E, Kent S B. Automated chemical synthesis of a protein growth factor for hemopoietic cells, interleukin-3. Science Jan. 10, 1986; 231 (4734):134–9).

In particular, the peptides were synthesized using an Applied Biosystems 430A Automated Synthesizer following manufacturer's instructions. Synthesized peptides were cleaved from the resin and deblocked using hydrofluoric acid following standard procedure as indicated above. After neutralization with sodium hydroxide to pH 7, the peptides were dialyzed into ammonium carbonate buffer and then lyophilized. Sequence was confirmed by peptide composition analysis.

The invention is illustrated in the below Examples, but it should be understood that the detailed description and specific examples, while indicating preferred embodiments of the invention, are given by way of illustration only, since various changes and modifications within the spirit and scope of the invention will become apparent to those skilled in the art from the detailed description.

In the Examples the following abbreviations of the amino acids are used:

Ala=Alanine
Arg=Arginine
Asn=Asparagine
Asp=Aspartate
Cys=Cysteine
Glu=Glutamate
Gly=Glycine
His=Histidine
Ile=Isoleucine
Leu=Leucine
Lys=Lysine
Met=Methionine
Phe=Phenylalanine
Pro=Proline
Ser=Serine Thr=Threonine
Trp=Tryptophan
Tyr=Tyrosine
Val=Valine

EXAMPLES

Example 1

Peptide synthesis and preparation of antisera.

Peptides corresponding to specific domains of the 91 kDa cytochrome $b_{558}$ subunit were prepared as described by Barany et al., Int. J. Pept. Protein Res., 30, 705–739 (1987). The peptides were checked for purity by reverse phase HPLC and amino acid composition analysis. The peptides studied to date were derived from the predicted amino acid sequence of the large subunit of human cytochrome $b_{558}$ based upon published cDNA sequences of the mRNA coding for this protein. One peptide of 20 amino acids in length is composed of the following linear sequence of residues with all of the properties as described above: Cys-Ser-Asn-Ser-Glu-Ser-Gly-Pro-Arg-Gly-Val-His-Phe-Ile-Phe-Asn-Lys-Glu-Asn-Phe. The cystine at the aminoterminal end of this peptide is not part of the intrinsic structure of the large subunit of the cytochrome $b_{558}$ and indicates that the addition of additional amino acids or other chemical groups to the 19 amino acid carboxyl-terminus of the cytochrome will not significantly alter its functional properties. (This peptide is called peptide No. 1.) A second peptide (peptide No. 2) with the sequence Cys-Ser-Asn-Pro-Arg-Gly-Val-His-Phe-Ile-Phe-Asn-Lys-Glu-Asn-Phe is also active and consists of the last 13 carboxylterminal peptides of the large subunit of human cytochrome $b_{558}$ to which have been added three amino acids Cys-Ser-Asn at the amino terminus to facilitate sulfhydryl mediated conjugation to keyhole limpet hemocyanin for antibody production. Antiserum CT4346 used in these studies was generated in New Zealand white rabbits by subcutaneous injection of the 13 amino acids containing peptide keyhole limpet hemocyanin conjugate in complete Freund's adjuvant followed by booster injection of the peptide conjugate in incomplete Freund's adjuvant at two weeks and again at one month. Antiserum CT4346 recognizes the large subunit of cytochrome $b_{558}$ as demonstrated in the results section. This indicates that substituted peptides which include the 13 carboxyl-terminal residues of the cytochrome are also active. (Of note is that immunization of rabbits with conjugates of peptides of 8 amino acid units failed to induce detectable antibody to cytochrome large subunit.)

Example 2

Evidence for a functional role for the cytoplasmic carboxylterminal domain of cytochrome $b_{558}$-91 kDa subunit.

The localization of the hydrophilic carboxyl-terminal domain of the –91 kDa cytochrome $b_{558}$ subunit to the cytoplasmic aspect of the plasma membrane suggested the potential for interaction of this domain with cytosolic or other membrane anchored components of the respiratory burst oxidase. Accordingly, measurements were carried out on the effects of antiserum or free carboxyl-terminal peptide on superoxide production in an arachidonate-activated cell-free system requiring components of cytosol and plasma membrane (Nunoi, H., Rotrosen, D., Gallin, J. I., and Malech, H. L. (1988) Science 242, 1298–1301; Bromberg, Y., and Pick, E. (1985) J. Biol. Chem. 260, 13539–13545).

Figure 2:
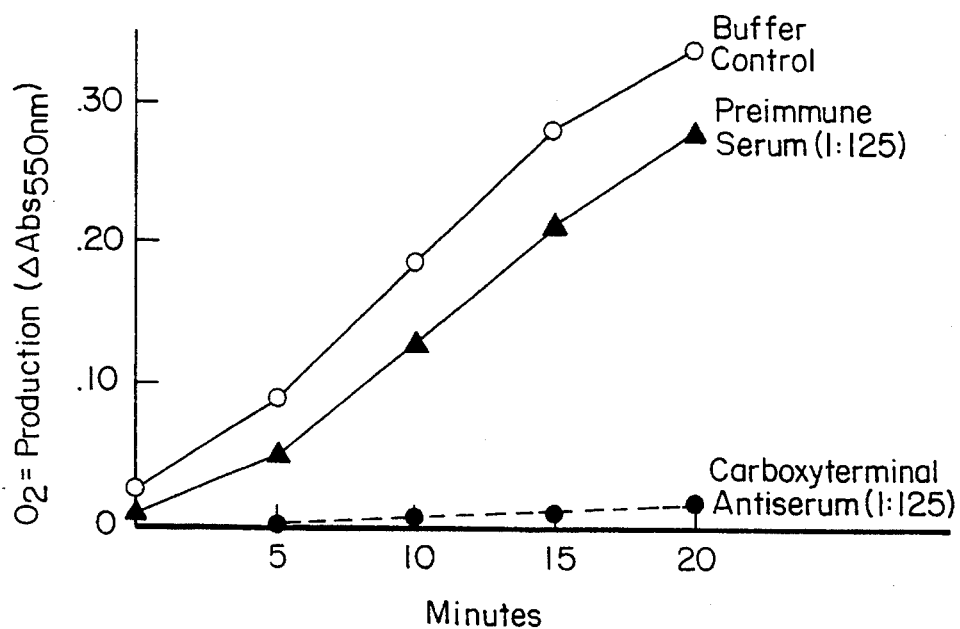

Preincubation of membrane with antiserum before dilution into the final reaction mixture was accompanied by a concentration dependent inhibition of NADPH oxidase activity with antiserum raised against carboxyl-terminal peptide, but not with preimmune serum (FIGS. 1 and 2). In two similar experiments, at the highest antiserum concentration tested, the rate of superoxide production was inhibited 78–94%, relative to a preimmune serum control.

Figure 3:
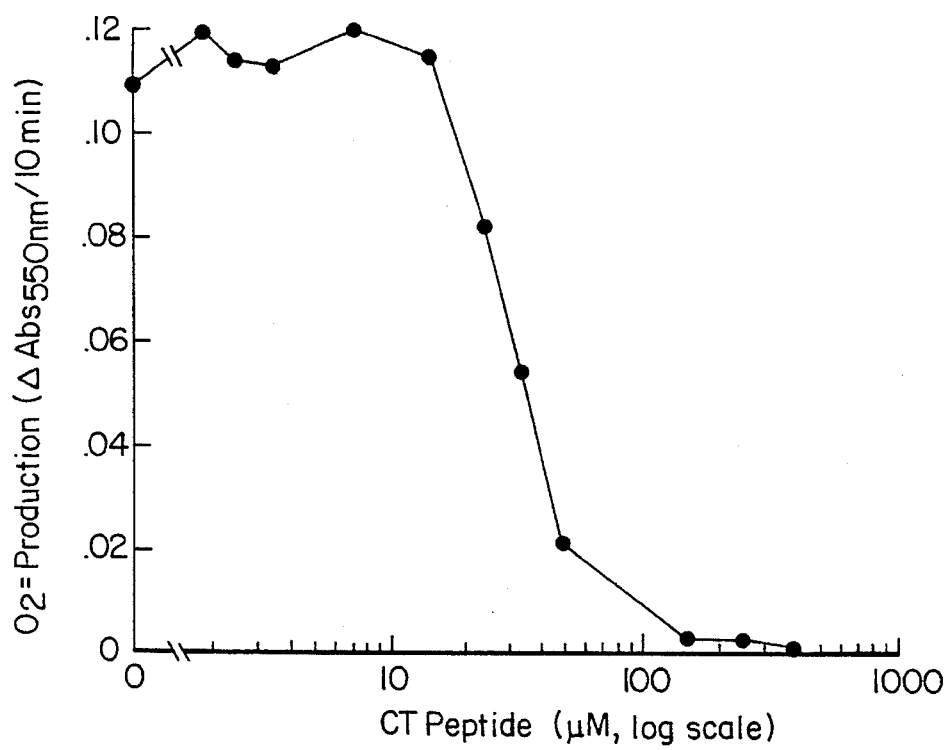

Carboxyl-terminal peptide No. 1 (the 19 amino acid synthetic peptide, residue 552–570, coupled to cysteine) blocked superoxide production in a concentration-dependent fashion (FIG. 3). At maximally inhibitory concentrations superoxide production was inhibited 100%, with a half-maximal inhibitory concentration of 35 µM. Carboxyl-terminal peptide No. 2 (which contains the 13 most carboxyl-terminal amino acids in correct sequence) also inhibited superoxide production with a similar $IC_{50}$ (not shown). In contrast, various irrelevant peptides did not significantly inhibit, or inhibited NADPH oxidase activity only slightly, over a similar concentration range (Table 1).

TABLE 1

INHIBITION OF NADPH OXIDASE ACTIVITY BY CYTOCHROME b558 91 kDa SUBUNIT CARBOXYL-TERMINAL PEPTIDE

| Peptide/ source | Sequence | Concentration (µM) | % inhibition* |
| --- | --- | --- | --- |
| cytochrome b558 ≈91 kDa subunit | | | |
| carboxyl-terminus | C-SNSEGPRGVHFIFNKENF | 250 | 100 |
| | | 150 | 99 |
| aminoterminus | GNWAVNEG-C | 150 | 8 |
| IL-1 | VFSMFQGEES | 200 | –6 |
| IL-1 | AENMFVFLGG | 200 | 7 |
| CR-1 | C-QTNEENSRVLP | 250 | 18 |
| CR-3 | C-TTTVMNPKFAES | 250 | 27 |
| Mannose-6-phosphate receptor | C-DDSDDDLLHI | 250 | 18 |

*Data are means of duplicate determinations in a single experiment representative of at least two experiments performed except with CR-1, CR-3, and mannose-6-phosphate receptor peptides (single experiments). Percent inhibition is calculated from the maximal linear rate of superoxide dismutase inhibitable ferricytochrome c reduction in the presence or absence of synthetic peptide added at the same time as the stimulus (30 µM arachidonic acid).

Figure 4:
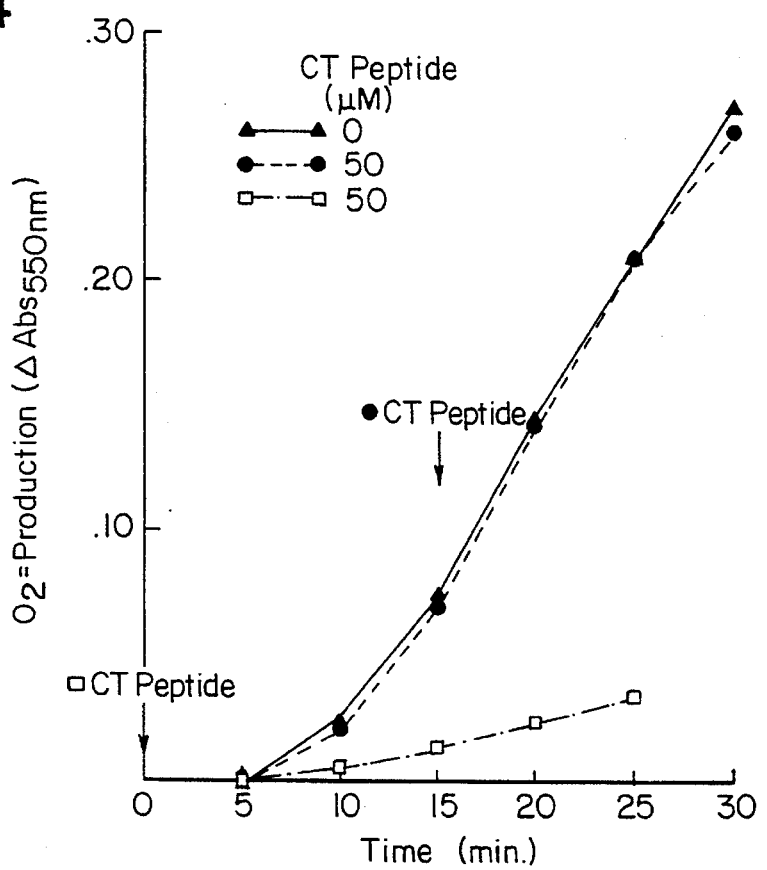

Addition of carboxyl-terminal peptide after "activation", during the linear phase of superoxide production, was not accompanied by demonstrable changes in the rate or total duration of subsequent superoxide production (FIG. 4). In contrast, addition of fatty acid-free bovine serum albumin (which binds free arachidonate) during the linear phase of superoxide production inhibits continued oxidase activity (not shown), excluding the trivial explanation that carboxyl-terminal peptide acts simply by binding free arachidonate.

The enclosed drawing (FIGS. 3 and 4) illustrates the inhibition of the superoxide production caused by the peptide derivatives according to the invention compared with the missing activity of another peptide derivative. It is demonstrated in the figure that the peptide Cys-Ser-Asn-Pro-Arg-Gly-Val-His-Phe-Ile-Phe-Asn-Lys-Glu-Asn-Phe (abbreviated CTP in this figure) used in the concentrations shown in a cell-free assay of superoxide production employing human neutrophil membranes and cytosol inhibits superoxide production (expressed as a change in light absorbance of the indicator, ferricytochrome C, at 550 nm) in a dose dependent fashion. The results of a similar assay with peptide Cys-Ser-Asn-Ser-Glu-Ser-Gly-Pro-Arg-Gly-Val-His-Phe-Ile-Phe-Asn-Lys-Glu-Asn-Phe yielded the same inhibition curve. A peptide corresponding to a distinctly different N-terminal portion of the large subunit of cytochrome $b_{558}$ (NTP) had no inhibitor activity indicating that the special region of the cytochrome corresponding to the peptides according to the instant invention are endowed with unique properties capable of inhibiting the oxidative burst of human neutrophils and other phagocytic cells.

We claim:

1. A peptide which blocks superoxide production in phagocytic cells which has 6–30 amino acid residues and which is from a domain of the 91 kDa subunit of human cytochrome $b_{558}$, wherein said domain is from the carboxyl-terminal peptide portion of the molecule.

2. The peptide of claim 1, which has a sequence of 13–19 amino acids and which is from a domain of the carboxyl-terminal peptide portion of the 91 kDa subunit of human cytochrome $b_{558}$.

3. A peptide as claimed in claim 1 which has 13–20 amino acid residues.

4. The peptide of claim 1, which has the amino acid sequence Pro-Arg-Gly-Val-His-Phe-Ile-Phe-Asn-Lys-Glu-Asn-Phe.

5. The peptide of claim 1, which has the amino acid sequence Ser-Asn-Ser-Glu-Ser-Gly-Pro-Arg-Gly-Val-His-Phe-Ile-Phe-Ile-Phe-Asn-Lys-Glu-Asn-Phe.

6. A peptide as claimed in claim 1 which further contains at least one substituent on the amino acid residues selected from a group of chemical moieties which will enhance the penetration of the peptide into phagocytic cells.

7. A peptide as claimed in claim 6 wherein the chemical moiety which will enhance the penetration of the peptide into phagocytic cells is selected from hydrophilic and amphophilic chemical groups.

8. A peptide as claimed in claim 7 wherein the chemical moiety which will enhance the penetration of the peptide into phagocytic cells is a cleavable ester-linked group.

9. A method for directly inhibiting activation of the specific enzyme systems involved in the oxidative burst of human phagocytic cells which comprises administering an effective amount of the peptide as claimed in claim 1 to a patient in need of such treatment.

10. A method for preventing or decreasing the tissue damage caused by phagocytic oxidative burst which comprises administering an effective amount of the peptide as claimed in claim 1 to a patient in need of such treatment.

11. A method for preventing or decreasing symptoms of gout, autoimmune disorders, myocardial infarction, adult respiratory distress syndrome, asthma and certain dermatological disorders which comprises administering an effective amount of the peptide as claimed in claim 1 to a patient in need of such treatment.

12. A peptide as claimed in claim 8 wherein the cleavable ester-linked group is an acetoxymethylester.

13. A pharmaceutical composition comprising a peptide which has 6–30 amino acid residues corresponding to a domain of the 91 kDa subunit of a human cytochrome $b_{558}$ which blocks superoxide production in phagocytic cells, wherein said domain is from the carboxyl-terminal peptide portion of the molecule; and a pharmaceutically acceptable carrier.

14. A pharmaceutical composition as claimed in claim 13 wherein the peptide has a sequence of 13–19 amino acids which is identical to a domain of the carboxyl-terminal peptide portion of the 91 kDa subunit of human cytochrome $b_{558}$.

15. A pharmaceutical composite on as claimed in claim 13 in which the amino acid sequence has 13–20 amino acid residues.

16. A pharmaceutical composition as claimed in claim 13 wherein the peptide has the amino acid sequence Pro-Arg-Gly-Val-His-Phe-Ile-Phe-Asn-Lys-Glu-Asn-Phe.

17. A pharmaceutical composition as claimed in claim 13 wherein the peptide has the amino acid sequence Ser-Asn-Ser-Glu-Ser-Gly-Pro-Arg-Gly-Val-His-Phe-Ile-Phe-Asn-Lys-Glu-Asn-Phe.

* * * * *